US00PP16933P2

(12) United States Plant Patent
Utecht

(10) Patent No.: US PP16,933 P2
(45) Date of Patent: Aug. 1, 2006

(54) *PELARGONIUM* PLANT NAMED 'FISROCCAL'

(50) Latin Name: *Pelargonium×hortorum*
Varietal Denomination: Fisroccal

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 22 days.

(21) Appl. No.: 11/167,836

(22) Filed: Jun. 27, 2005

(51) Int. Cl.
*A01H 5/00* (2006.01)

(52) U.S. Cl. ..... Plt./327

(58) Field of Classification Search ..... Plt./327
See application file for complete search history.

*Primary Examiner*—Kent Bell
(74) *Attorney, Agent, or Firm*—Jondle & Associates P.C.

(57) ABSTRACT

A new cultivar of *Pelargonium* particularly characterized by having salmon-orange, semi-double flowers, large inflorescences, long and strong peduncles, medium green foliage with weak zonation, a round, bushy plant habit with vigorous growth, and a mid-season flowering response is disclosed.

1 Drawing Sheet

Figure 1:
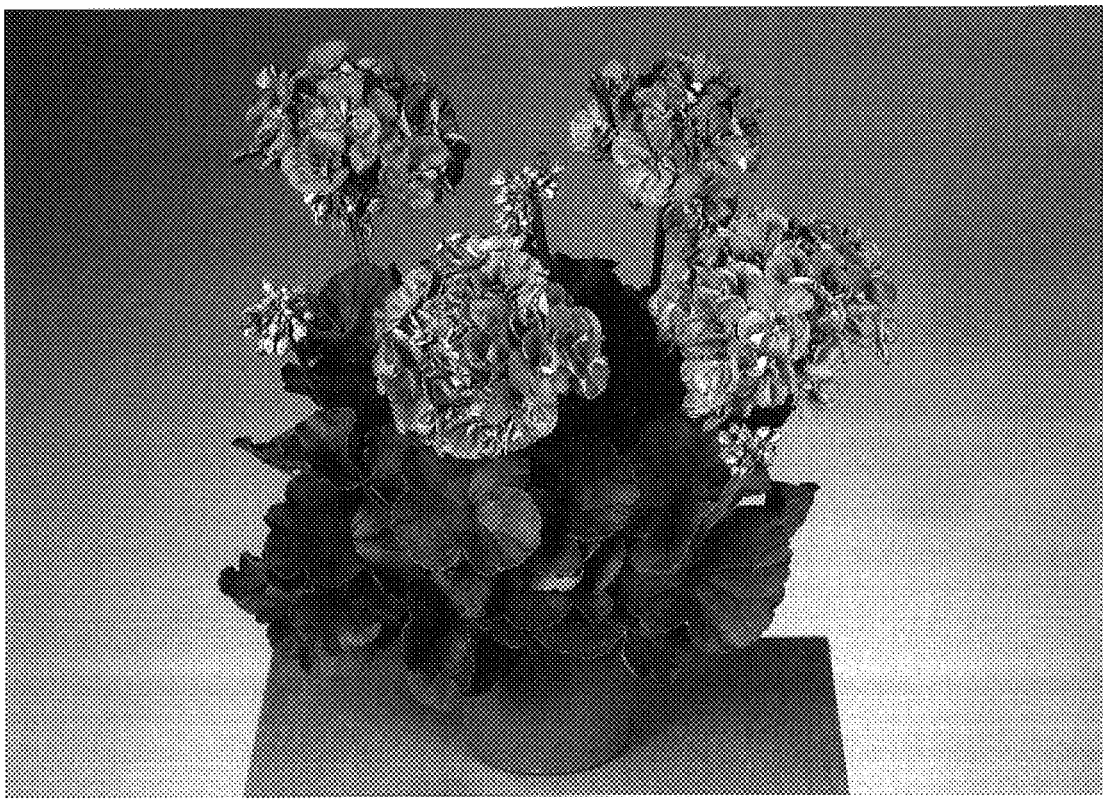

Genus and species: *Pelargonium×hortorum.*
Variety denomination: 'Fisroccal'.

BACKGROUND OF THE NEW PLANT

The present invention comprises a new and distinct cultivar of *Pelargonium*, botanically known as *Pelargonium× hortorum*, a hybrid of *Pelargonium zonale* L'Héritier and hereinafter referred to by the cultivar name 'Fisroccal'. The new cultivar is a product of a planned breeding program which had the objective of creating new varieties having orange semi-double flowers, deep green zonation of foliage, and a vigorous but well-branched growth habit. 'Fisroccal' was discovered as a seedling resulting from a cross between the female parent, 'Fip 440' (U.S. Plant Pat. No. 13,964), which has orange-red semi-double flowers, medium green foliage with distinct zonation, and a vigorous growth habit and the male parent, 'Dueimap' (U.S. Plant Pat. No. 13,241), which has bright orange, semi-double flowers, grass-green foliage without or with very slight zonation, and a medium-sized plant habit.

The new cultivar was created in 2000 in Hillscheid, Germany, and has been asexually reproduced repeatedly by vegetative cuttings in Galdar, Gran Canaria, Spain, and Hillsheid, Germany, over a four-year period. 'Fisroccal' has not been observed under all possible environmental conditions, thus, the phenotype may vary significantly with variations in the environment such as temperature, light intensity, and day length. It has been found to retain its distinctive characteristics through successive asexual propagations. 'Fisroccal' reproduces true to type in successive generations of asexual reproduction.

Plant Breeder's Rights for this cultivar were applied for in Germany on Jun. 2, 2004. No sales or offers for sale of this cultivar have been made before early July 2004.

SUMMARY OF THE INVENTION

The following are the most outstanding and distinguishing characteristics of this new cultivar when grown under normal commercial practices in Hillscheid, Germany.

1. Salmon-orange, semi-double flowers with good stability of flower color;
2. Large inflorescences on long, strong peduncles;
3. Medium-green foliage with weak zonation;
4. Tall, moderately tight plant habit with vigorous growth;
5. A mid-season flowering response; and
6. Fair rain resistance.

DESCRIPTION OF PHOTOGRAPH

This new *geranium* plant is illustrated by the accompanying photograph which shows blooms, buds, and foliage of the plant; the colors shown are as true as can be reasonably obtained by conventional photographic procedures. The photograph is of a twelve-week-old plant grown from rooted cuttings, grown in 14-cm pots, left un-pinched, and grown under greenhouse conditions which approximate those generally used in commercial practice.

FIG. 1. shows overall plant habit with blooms, buds, and foliage.

DESCRIPTION OF THE NEW CULTIVAR

The following detailed descriptions set forth the distinctive characteristics of 'Fisroccal'. The data which define these characteristics were collected from asexual reproductions carried out in Hillscheid, Germany. The plant history was taken on twelve-week-old, un-pinched plants grown in 14-cm pots in a greenhouse during mid-May. The color readings were determined under natural light in mid-May from flowers grown in a greenhouse. Color references are to The R.H.S. Colour Chart of The Royal Horticultural Society of London (R.H.S.) (2001).

DETAILED BOTANICAL DESCRIPTION

Classification:

*Botanical.*—*Pelargonium×hortorum*, a hybrid of *Pelargonium zonale* L'Héritier.

*Common name.*—*Geranium.*

*Parentage*.—Female parent: 'Fip 440' (U.S. Plant Pat. No. 13,964). Male parent: 'Dueimap' (U.S. Plant Pat. No. 13,241).

Plant:

*Branching habit*.—6.6 branches per plant.

*Height*.—19.8 cm for a 9 week-old plant (measured from base of stem to the tips of the branches, excluding the inflorescences).

*Width*.—26.5 cm for a 9 week-old plant.

*Time to produce a finished flowering plant*.—For spring flower response in Hillscheid, Germany, in 2004, 50% of the plant had open flowers after 9 weeks.

*Outdoor plant performance*.—Plants continuously flower; a flower count in mid-May of 2004 in Hillscheid, Germany indicated about 2 inflorescences per plant.

Leaves:

*Arrangement*.—Alternate.

*Immature leaf*.—Color: Upper surface: RHS 137D (medium-green). Lower surface: Between RHS 137D and RHS 143B.

*Mature leaf*.—Color: Upper surface: RHS 137C (medium-green). Lower surface: Between RHS 137D and RHS 143B. Length: 6.8 cm. Width: 10.6 cm.

*Zonation color*.—RHS 166A (brown) with a weak distinctness.

*Zonation diameter*.—Inner ring is 5.3 cm and zonation belt 2.3 cm wide.

*Apex*.—Rounded.

*Base*.—Cordate.

*Shape*.—Kidney-shaped with weak lobes and with the lowest lobes overlapping or forming a narrow gap.

*Margin*.—Bi-crenate and somewhat wavy.

*Texture*.—Upper surface is smooth and dull to slightly glossy.

Petioles:

*Length*.—6.0–8.0 cm.

*Diameter*.—0.3 cm.

*Color*.—RHS 143B to RHS 143C (light-green).

*Texture*.—Weak pubescence.

Stems:

*Length*.—7.0–9.0 cm.

*Internode length*.—1.5–2.5 cm.

*Color*.—RHS 143B (green).

*Texture*.—Slight pubescence.

Flower buds:

*Length*.—1.8 cm.

*Width*.—0.9 cm.

*Shape*.—Elliptical.

*Color of sepals (just before petals unfold)*.—RHS 144A (light-green).

*Color of petals (just before petals unfold)*.—RHS 41A to RHS 41B.

Inflorescence:

*Type*.—An umbel composed of 35–45 flowers.

*Umbel diameter*.—11.0 cm.

*Umbel depth (height)*.—7.0 cm.

*Umbel shape*.—Semi-spherical.

*Lastingness of umbel on the plant*.—About 18 days.

*Peduncle*.—Length: 19.2 cm. Diameter: 5.0–7.0 mm. Texture: Covered with weak pubescence. Color: RHS 143B (light-green).

*Pedicel*.—Length: 3.9 cm. Diameter: 1.0–2.0 mm. Texture: With weak pubescence. Color: RHS 143C (light-green) and RHS 179B to 179C (brown) infused at the upper end.

Corolla:

*Diameter*.—4.8 cm.

*Form*.—Semi-double.

*Shape*.—Zygomorphic, often with a gap between upper and lower petals.

*Number of petals*.—7–9.

*Petaloids*.—Number: 0–2. Shape: Narrow. Color: RHS 40A to RHS 40B.

*Lastingness of individuals flowers on the plant*.—8 days at 18° C.

*Fragrance*.—None.

Petals:

*Upper petals*.—Length: 3.0–3.2 cm. Width: 2.5–2.8 cm. Color: Upper surface: RHS 41A. Lower surface: RHS 43C. Markings: Has near base a weak macule between RHS 54A (pink) and RHS 57C (pink).

*Lower petals*.—Length: 2.7–2.8 cm. Width: 2.5–2.6 cm. Color: Upper surface: RHS 43C. Lower surface: RHS 43D. Markings: Absent.

*Shape*.—Obovate.

*Apex*.—Rounded.

*Base*.—Acute.

*Margin*.—Entire.

*Texture*.—Smooth and slightly glossy.

Sepals:

*Number*.—5.

*Length*.—1.0–1.2 cm.

*Width*.—0.4 cm for the largest upper sepal and 0.3 cm for the other sepals.

*Shape*.—Linear to lanceolate.

*Apex*.—Acute.

*Base*.—Truncate.

*Margin*.—Entire.

*Texture*.—Very weak pubescence.

*Color*.—For both upper and lower surfaces, RHS 144A to RHS 144B (light-green) and slightly RHS 179A (brown) near base.

Reproductive organs:

*Androecium*.—Number of anthers: 3–5. Filament color: RHS 155D (white) to RHS 41B (orange). Filament length: 5.0–7.0 mm. Pollen color: RHS 26A (yellow-orange). Pollen amount: Moderate.

*Gynoecium*.—Pistil number: 1. Pistil length: 7.0 mm. Stigma color: RHS 43D (salmon-pink). Stigma shape: 5–6 lobed. Style color: RHS 43D (salmon-pink). Style length: 3.0–4.0 mm. Style shape: Filament-like, with the lobes of the stigma horizontally directed, at right angles.

Fruit/seed set: A few seeds may occasionally develop, mainly from late summer to early fall.

Disease and insect resistance: Average and typical for the species, no observations made.

COMPARISON WITH KNOWN CULTIVARS

Of the many commercial cultivars known to the present inventor, the most similar in comparison to 'Fisroccal' are the related varieties 'Fip 440' (U.S. Plant Pat. No. 13,964) and 'Dueimap' (U.S. Plant Pat. No. 13,241) and the commercial variety 'Americana Coral' (U.S. Plant Pat. No. 7,934).

Cultivar 'Fisroccal' differs from the female parent variety 'Fip 440' (U.S. Plant Pat. No. 13,964) in that the flowers of 'Fisroccal' are lighter in color with a more salmon-colored hue and it has leaves with less distinct zonation.

Cultivar 'Fisroccal' differs from the male parent 'Dueimap' (U.S. Plant Pat. No. 13,241) in that the flower color of 'Fisroccal' has a less deep orange and more salmon hue than 'Dueimap'. Additionally, the foliage of 'Fisroccal' develops somewhat stronger zonation, it has larger umbels that are higher above the foliage, and the growth habit is generally more vigorous than that of 'Dueimap'.

Cultivar 'Fisroccal' differs from the commercial variety 'Americana Coral' (U.S. Plant Pat. No. 7,934) in that 'Fisroccal' has a flower color that is slightly more orange in hue, has slightly wider inflorescences, and has somewhat smaller leaves with weak zonation. Additionally, 'Americana Coral' exhibits either no zonation or zonation that is very weak on its immature leaves.

I claim:

1. A new and distinct cultivar of *Pelargonium* plant as shown and described herein.

* * * * *